United States Patent
Stutz et al.

[11] 4,000,139
[45] Dec. 28, 1976

[54] ORGANIC COMPOUNDS

[75] Inventors: Peter Stutz, Reinach; Paul Stadler, Biel-Benken, both of Switzerland

[73] Assignee: Sandoz Ltd., Basel, Switzerland

[22] Filed: July 2, 1974

[21] Appl. No.: 485,275

[30] Foreign Application Priority Data
July 9, 1973  Switzerland .............. 9954/73
Jan. 31, 1974  Switzerland .............. 1325/74

[52] U.S. Cl. .............. 260/268 TR; 260/285.5
[51] Int. Cl.² .............. C07D 295/04
[58] Field of Search .............. 260/268 TR, 268 PE

[56] References Cited
UNITED STATES PATENTS
3,314,959  4/1967  Hoffmann .............. 260/268 TR Primary Examiner—Donald G. Daus
Assistant Examiner—D. B. Springer
Attorney, Agent, or Firm—Gerald D. Sharkin; Robert S. Honor; Thomas O. McGovern

[57] ABSTRACT

The invention concerns a novel process for the production of a compound of formula I,

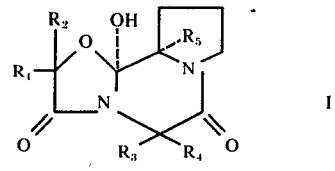

wherein
$R_1$ is the cyano group, or -COX, wherein X is the amino group or an -O-(lower)alkyl radical, and
$R_2$ to $R_5$ are substituents inert to internal cyclization conditions, comprising subjecting a compound of formula II,

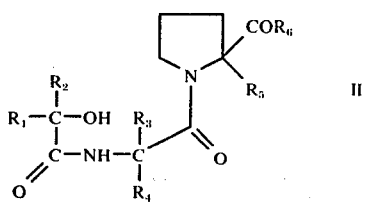

wherein the variables $R_1$ to $R_5$ are as defined above, and $R_6$ is a radical capable of leaving under the reaction conditions, to an intramolecular condensation in the presence of a base, the compounds of formula I being useful intermediates in the preparation of ergot alkaloids.

24 Claims, No Drawings

ORGANIC COMPOUNDS

IMPROVEMENTS IN OR RELATING TO ORGANIC COMPOUNDS

The present invention relates to novel octahydro-oxazolo[3,2-a]pyrrolo[2,1-c]pyrazine and related derivatives.

In accordance with the invention there are provided new compounds of formula I,

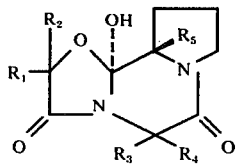

wherein $R_1$ is the cyano group, or -COX, wherein X is the amino group or an -O-(lower)alkyl radical, and $R_2$ to $R_5$ are substituents inert to internal cyclization conditions, e.g. known octahydro-oxazolo[3,2-a]pyrrolo[2,1-c]pyrazine substituents, e.g., wherein $R_2$ is lower alkyl, $R_3$ is hydrogen or lower alkyl, $R_4$ is hydrogen, lower alkyl, phenyl, benzyl, or benzyl monosubstituted by lower alkoxy, and $R_5$ is hydrogen or lower alkyl.

The O-(lower)alkyl radical of the -COX definition of $R_1$ may, for example, contain 1 to 6 carbon atoms, preferably 1 to 4 carbon atoms and especially 1 or 2 carbon atoms.

The lower alkyl groups $R_2$, $R_3$ and $R_5$ may, for example, contain up to 5 carbon atoms, preferably 1 to 4 carbon atoms.

When $R_3$ and $R_5$ are lower alkyl groups, these especially signify the methyl group.

The lower alkyl group in the definition of $R_4$ may, for example, contain up to 6 carbon atoms, preferably 1 to 4 carbon atoms. The (lower)alkoxy group mentioned as possible substituent of a benzyl group $R_4$ preferably contains 1 to 4 carbon atoms and especially signifies the methoxy group, e.g. in the para-position.

Any carbon-containing radical not otherwise particularly defined preferably has up to 6 carbon atoms.

Further, in accordance with the invention a compound of formula I may be obtained by a process comprising subjecting a compound of formula II,

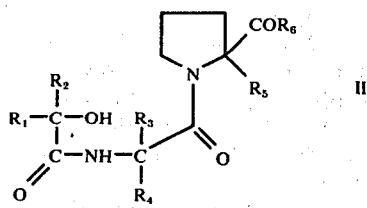

wherein the variables $R_1$ to $R_5$ are as defined above, and $R_6$ is a radical capable of leaving under the reaction conditions, to an intramolecular condensation in the presence of a base.

$R_6$ may be a substituted or unsubstituted phenyloxy or phenylthio radical. Suitable substituents include nitro, lower alkyl or halogen such as chlorine and fluorine.

Examples of suitable $R_6$ groups are pentafluoro or pentachlorophenoxy, a phenylthio or p-chlorophenylthio radical, nitrophenoxy, or nitrophenoxy mono- or disubstituted by nitro and/or methyl or chlorine.

$R_6$ may also be N-succinimidoxy.

For this reason it is preferred to use compounds of formula II containing as leaving group $R_6$ an o,p-dinitrophenoxy, an o-methyl-o;p-dinitrophenoxy, a pentachlorophenoxy or especially a p-nitrophenoxy radical.

Reaction parameters, e.g. temperature, solvent, base, may vary within wide limits readily determined in conventional manner.

Thus, the base or base strength used is especially dependent on the solvent chosen; whereas strong bases may be used in an anhydrous, aprotic medium, the cyclization in an aqueous medium is conveniently effected under mild conditions, since otherwise the compounds of formula I are directly saponified to the corresponding compounds of formula I wherein $R_1$ is the carboxyl group, and the acids can only be isolated from the reaction mixture with great difficulty.

The cyclization in accordance with the invention is conveniently effected in a polar solvent. Examples of suitable aprotic, polar solvents are dimethyl sulphoxide, hexamethyl phosphoric acid triamide, acetonitrile, and di(lower)alkylamides of an organic carboxylic acid, such as dimethyl formamide or dimethylacetamide.

Strong bases which may be used for the cyclization in an anhydrous, aprotic medium are bases capable of deprotonizing the nitrogen atom adjacent to $=CR_3R_4$, and which do not enter into a reaction with carbonyl groups, e.g. alkali metal hydrides such as sodium hydride, and alkali metal alcoholates such as sodium ethylate. When an alkali metal alcoholate is used as base and X signifies lower alkoxy, it is convenient to use the alcoholate corresponding to the alcohol HX (otherwise possible interchange of ester radicals). For a similar reason (otherwise possible reaction $R_2 = CO(lower)$ alkoxy to $R_1 = CONH_2$) it is not convenient to use an alkali metal amide as base when $R_1$ is -CO(lower)alkoxy. In this process variant it is convenient to use 1 to 1.5 mols of a strong base for every mol of a compound of formula II.

When the cyclization is effected in an aqueous medium, it is convenient to use aids to solution.

Examples of suitable inert, water-miscible solvents are: dimethyl sulphoxide, dimethoxyethane, open chain or cyclic ethers such as dioxane or tetrahydrofuran, and di(lower)alkylamides of an organic carboxylic acid, such as dimethyl formamide or dimethylacetamide.

In an aqueous medium it is preferable to carry out the reaction under weakly basic conditions, especially at a pH value of 8 to 10.

A borate, carbonate or phosphate solution with hydroxyl ions may, for example, be used as aqueous buffer solution. Especially suitued is the use of a borate buffer (pH = 9) with the addition of catalytic amounts of 2-hydroxypyridine.

Preferred reaction temperatures are between about 0° and 30° C. The reaction is preferably effected at room temperature. When an anhydrous medium is used, stirring or other agitation is preferably effected.

The reaction time is dependent on the reaction conditions and on the significance of the substituents in formula II; it may range from about 1 to 10 hours for satisfactory yields.

The working up of the resulting reaction mixture for the isolation of the desired final products may be effected in known manner, e.g. by extraction and optionally subsequent chromatography.

The starting materials of formula II are new, and their production is also included in the present invention.

Compounds of formula II may be obtained by reacting an acid of formula III,

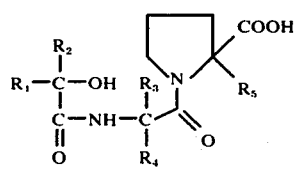

wherein the variables $R_1$ to $R_5$ are as defined above, with a compound of formula IV, $$R_6H \qquad \text{IV}$$

wherein $R_6$ is as defined above, or with a compound of formula IVa,

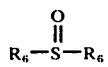

wherein $R_6$ is as defined above.

The reaction of a compound of formula III with a compound of formula IV or IVa may be effected in known manner. The reaction with a compound of formula IV may, for example, be effected in the presence of dicyclohexylcarbodiimide. An excess of a compound of formula IV is preferably used. The reaction with a compound of forumula IVa may, for example, be effected in the presence of a week tertiary organic base such as pyridine or a homologue thereof.

The resulting compounds of formula II may be isolated from the reaction mixture in known manner.

The compounds of formula III, which are likewise new, may be obtained by debenzylating a compound of formula V,

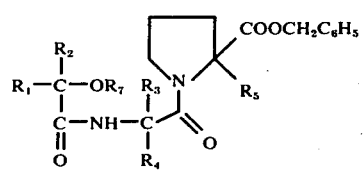

wherein the variables $R_1$ to $R_5$ are as defined above, and $R_7$ is hydrogen or benzyl.

The debenzylation of the compounds of formula V may be effected in known manner. The hydrogenolytic removal of the benzyl group(s) is preferably effected by hydrogenation in the presence of a noble metal catalyst, preferably palladium, on a suitable carrier such as charcoal. Examples of solvents which may be used are glacial acetic acid or ethanol or a mixture of both solvents, but preferably ethyl acetate, especially for the debenzylation of the compounds of formula V wherein $R_2$ is an isopropyl group.

Compounds of formula V may, for example, be obtaind by condensing a tartronic acid derivative of formula VI,

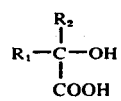

wherein $R_1$ and $R_2$ are as defined above, or of formula VII,

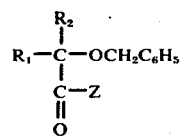

wherein $R_1$ and $R_2$ are as defined above, and

Z is an active acid component, e.g. halogen, preferably chlorine, with an aminoacid benzyl ester of formula VIII,

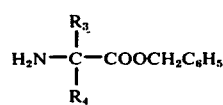

wherein $R_3$ and $R_4$ are as defined above, in accordance with the usual methods in peptide chemistry, e.g. with carbodiimide synthesis for compounds of formula VI or preferably in the case of both compounds of formula VI and compounds of formula VII, in the presence of N-ethyldiisopropylamine, in the presence of a suitable solvent, e.g. methylene chloride/-dioxane or dimethoxyethane. The benzyl-protective group(s), i.e. either ester-benzyl and any ether-benzyl which may be present are subsequently removed simultaneously, or selectively only the ester-benzyl, from the resulting compound of formula IX,

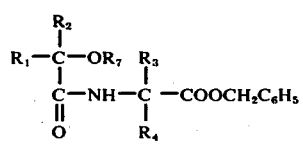

wherein the variables $R_1$ to $R_4$ and $R_7$ are as defined above, in known manner by hydrogenolysis, preferably by catalytic hydrogenation with palladium on charcoal, e.g. in glacial acetic acid or ethanol or a mixture of both solvents, but preferably in ethyl acetate, especially in the case of a compound of formula IX wherein $R_2$ is isopropyl, and the resulting free acid of formula X,

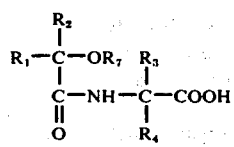

wherein the variables
R₁ to R₄ and R₇ are as defined above,
is condensed with a compound of formula XI,

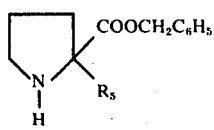

wherein $R_5$ is as defined above,
in accordance with the usual methods in peptide chemistry, e.g. by carbodiimide synthesis, in the presence of a suitable solvent, e.g. methylene chloride, dioxane, ethyl acetate or dimethoxyethane, at room temperature, whereby at least an equimolar amount of 1-hydroxybenzotriazol may preferably be added in order to minimize racemization.

Some of the compounds of formula I, produced in accordance with the invention, are new. The new compounds are indicated in the following Table:

| Formula | Compounds of formula 1 | | | | |
|---|---|---|---|---|---|
| | $R_1$ | $R_2$ | $R_3$ | $R_4$ | $R_5$ |
| Ia | CN CONH₂ | a.sig. | a.sig. | a.sig. | a.sig. |
| Ib | COOAlkyl** | a.sig.* | a.sig. | H, alkyl, phenyl, alkoxybenzyl | Alkyl |
| Ic | COOAlkyl | Alkyl with more than 1 C | a.sig. | Benzyl | CH₃ |
| Id | COOAlkyl | CH₃ | Alkyl | Benzyl | CH₃ |
| Ie | COOAlkyl | CH₃ | H | Benzyl | Alkyl with more than 1 C |
| If | COOAlkyl | Alkyl | Alkyl | (lower)alkoxy-benzyl | H |
| Ig | COOAlkyl | Alkyl with more than 2 C | H | (lower)alkoxy-benzyl | H |
| Ih | COOAlkyl | CH₃ | H | Benzyl monosubstituted by (lower)alkoxy with at least 2 C, o-methoxybenzyl m-methoxybenzyl | H |
| Ik | COOCH₃ or COOAlkyl (Alkyl = lower alkyl with at least 3 C) | CH₃ | H | p-methoxybenzyl | H |

*a.sig.: the significance indicated above for this compound.
**Alkyl signifies (lower)alkyl.

The compounds of formulae Ia, Ib, Ic, Id, Ie, If, Ig, Ih and Ik are also included in the present invention.

The synthesis of compounds of formula I is of significance in view of the synthetic production of peptide alkaloids of the ergot type. In the compounds of formula I the radical $R_1$ = COO(lower)alkyl may be converted into an amino group in accordance with known methods. The conversion of compounds of formula I wherein $R_1$ is the carboxamido or cyano group, into the corresponding amino compounds may likewise be effected in accordance with known methods. The reaction of salts of 2-amino derivatives of compounds of formula I with lysergic acid may be effected in known manner to produce known ergot alkaloids of known activity.

The starting materials are known or may be produced in accordance with known methods, or in a manner analogous to the methods described herein or to known methods.

In the following non-limitative Examples all temperatures are indicated degrees Centegrade.

EXAMPLE 1

2-carbethoxy-2-methyl-5-benzyl-10b-hydroxy3,6-dioxo-octahydro-8H-oxazolo[3,2-a]-pyrrolo[2,1-c]pyrazine 5 g of Linde molecular sieve (3A) are added at room temperature to 10.54 g (20 millimols) of N-(2R-hydroxy-2-carbethoxy-propionyl)-L-phenylanyl-L-proline-p-nitrophenyl ester in 250 cc of absolute dimethyl formamide and stirring is effected for 15 minutes. 25 millimols of sodium hydride (e.g. 950 mg of a 63 % oily suspension) are then added and stirring is continued for 2 hours at room temperature in the absence of moisture. Working up is effected by removing most of the solvent by distillation in a high vacuum, decomposing the residue with about 50 cc of ethanol while cooling strongly and pouring immediately into a cooled 1 normal soda solution. The reaction mixture is extracted well with chloroform and washed twice with a 1 normal soda solution. After drying over sodium sulphate and removing the solvent by evaporation, a crystalline crude product is obtained, from which the title compound is obtained in the form of colourless needles by cruystallization from isopropyl ether; M.P. 134°–136°; $[\alpha]_D^{20} = -25.2°$ (c = 1.5 in ethanol).

The N-(2R-2-hydroxy-2-carbethoxy-propionyl)-L-phenylalanyl-L-proline-p-nitrophenyl ester, used as starting material, may, for example, be produced as follows:

a.

N-(2R-2-benzyloxy-2-carbethoxy-propionyl)-L-phenylalanine-benzyl ester 12.9 cc (75 millimols) of N-ethyldiisopropylamine are added at 0° to 12.75 g (50 millimols) of L- phenylalanine-benzyl ester in 250 cc of absolute methylene chloride. A solution of 13.5 g (50 millimols) of S-(+)-methyl-benzyloxy-malonic acid monoethyl ester chloride in 50 cc of absolute methylene chloride is subsequently added dropwise with stirring, and stirring and continued at 0° for one hour. Working up is effected by washing the reaction mixture in the cold with a saturated sodium bicarbonate solution. Extraction with methylene chloride, drying over sodium sulphate and evaporation of the solvent yield the title compound as oily residue which is immediately used for the next reaction. $[\alpha]_D^{20} = +39°$ (c = 2 in chloroform).

b. N-(2R-2-hydroxy-2-carbethoxy-propionyl)-L-phenylalanine

The benzyl protective radicals are split off by dissolving the oily residue obtained in step (a) above in 450 cc of ethyl acetate and hydrogenating with 10 g of palladium/charcoal (10 % palladium catalyst) at normal pressure and room temperature. After 8 to 16 hours, about 2.2 liters of hydrogen have been taken up. Filtration is effected and after concentrating the filtrate the title compound is obtained as colourless resin.

Brucine salt: from absolute ethyl acetate; M.P. 110°–112°; $[\alpha]_D^{20} = +29.8°$ (c = 1 in chloroform).

c. N-(2R-2-hydroxy-2-carbethoxy-propionly)-L-phenylalanyl-L-proline-benzyl ester 14 g of the resin obtained in step (b) above are dissolved in 300 cc of ethyl acetate at room temperature and after the addition of 13.5 g (0.1 mol) of 1-hydroxy-benzo-triazole (dry or moistened) stirring is effected for 10 minutes. 10.3 g (50 millimols) of dicyclohexyl-carbodiimide are then added to the almost clear solution and stirring is effected for a further 10 minutes. 10.3 g (50 millimols) of L-proline-benzyl ester in 50 cc of ethyl acetate are finally added dropwise within 5 minutes and stirring is effected for a further 90 minutes. After removing the precipitate by filtration, the filtrate is concentrated by evaporation and the residue is taken up in ether in order to remove the last traces of dicyclohexylcarbodiimide by crystalization. The filtrate is washed with cold 1 normal hydrochloric acid, a sodium bicarbonate solution and ice water. After drying over sodium sulphate and removing the solvent by distillation, the title compound is obtained as a resinous residue.

d. N-(2R-2-hydroxy-2-carbethoxy-priopionyl)-L-phenylalanyl-L-proline

The ester obtained in step (c) is dissolved in 300 cc of ethyl acetate and hydrogenated as described in step (b) with 5 g of palladium/charcoal (10% palladium). After working up in analogous manner, a colourless resin is obtained, which is used as such for the next reaction step.

e. N-(2R-2-hydroxy-2-carbethoxy-propionyl)-L-phenylalanyl-L-proline-p-nitrophenyl ester 16.5 g of acid obtained in step (d) above are dissolved in 400 cc of ethyl acetate, and 13.9 g (0.1 mol) of p-nitro-phenol and 10.3 g (0.05 mols) of dicyclohexyl-carbodiimide are successively added. After stirring at room temperature for one hour, filtration is effected and the filtrate is concentrated by evaporation. The residue is dissolved in chloroform and thoroughly washed with a 1 normal soda solution and a sodium bicarbonate solution. After drying over sodium sulphate and evaporating the solvent, the initially oily title compound crystallizes from methylene chloride/isopropyl ether. Yellowish crystals are obtained, which are dissolved in ethyl acetate for further purification. The insoluble component is removed by filtration, careful evaporation is effected and crystallization is again effected from isopropyl ether. After drying at 60° in a high vacuum, light yellowish crystals, having a M.P. of 121°–123°; $[\alpha]_d^{20} = -60°$ (c = 1, chloroform), are obtained.

EXAMPLE 2

2-carbethoxy-2-methyl-5-benzyl-10b-hydroxy3,6-dioxo-octahydro-8H-oxazolo[3,2-a pyrrolo[2,1-c]pyrazine Proceeding in a manner analogous to that described in Example 1 and by cyclization of N-(2R-hydroxy-2-carbethoxy-propionyl)-L-phenylalanyl-L-proline-2,4-dinitrophenyl ester (M.P. 152°–155° (ether); $[\alpha]_D^{20} = -64°$ (c= 1 chloroform) the title compound is obtained; M.P. 134°–136°; $[\alpha]_D^{20} = -25,2°$ (c = 1,5 in ethanol).

The ester used as starting material, is obtained in a manner analogous to that described in step (e) of Example 1, by using 0,1 mol (18,4 g) 2,4-dinitrophenol instead of p-nitro-phenol.

EXAMPLE 3

2-carbethoxy-2-methyl-5-benzyl-10b-hydroxy-3,6-dioxo-octahydro-8H-oxazolo[3,2-a]pyrrolo[2,1-c]pyrazine Proceeding in a manner analogous to that described in Example 1 and by cyclization of N-(2R-2-hydroxy-2-carbethoxy-propionyl)-L-phenylalanyl-L-proline-2,4-dinitro-6-methylphenyl ester (M.P. 140°–141°; ether); $[\alpha]_D^{20} = -38°$ (c = 1 in chloroform)) the title compound is obtained; M.P. 134°–136°; $[\alpha]_D^{20} = -25,2°$ (c = 1,5 in ethanol).

The ester used as starting material is obtained in a manner analogous to that described in step (e) of Example 1, by using 0,1 mol (19,8 lg) 4,6dinitro-o-cresol.

EXAMPLE 4

2-carbethoxy-2-methyl-5-benzyl-10b-hydroxy-3,6-dioxo-octahydro-8H-oxazolo[3,2-a]pyrrolo[2,1-c]pyrazine Proceeding in a manner analogous to that described in Example 1 and by cyclization of N-(2R-2-hydroxy-2-carbethoxy-propionyl)-L-phenylalanyl-L-proline-pentachlorophenyl ester (M.P. 140°–142° (ether/isopropyl ether); $[\alpha]_D^{20} = -27°$ (c = 1 in chloroform)) the title compound is obtained; M.P. 134°–136°; $[\alpha]_D^{20} = -25,2°$ (c = 1,5 in ethanol).

The ester used as starting material, is obtained in a manner analogous to that described in step (e) of Example 1,by using 26,6 g pentachlorophenol.

EXAMPLE 5

2-carbethoxy-2-isopropyl-5-benzyl-10b-hydroxy-3,6-dioxo-octahydro-8H-oxazolo[3,2-a]pyrrolo[2,1-c]pyrazine Proceeding in a manner analogous to that described in Example 1 and by cyclization of N-(2R-2-hydroxy-2-carbethoxy-isovaleryl)-L-phenylalanyl-L-proline-p- nitrophenyl ester, the title compound is obtained in crystalline form after chromatography on silica gel; M.P. 152°–154°; $[\alpha]_D^{20} = -17°$ (c = 1, ethanol).

The N-(2R-2-hydroxy-2-carbethoxy-isovaleryl)-L-phenylalanyl-L-proline and the p-nitrophenyl ester thereof, used as starting materials, are obtained in a manner analogous to steps (d) and (e) of Example 1. S-(+)-isopropyl-benzyloxymalonic acid monoethyl ester chloride is used as reaction component in step (a). The intermediates resulting in the individual steps cannot be obtained in crystalline form and the proline obtained in step (d) and the p-nitrophenyl ester obtained in step (e) are also converted as crude products.

EXAMPLE 6

2-carbethoxy-2,5-diisopropyl-10b-hydroxy-3,6-dioxo-octahydro-8H-oxazolo[3,2-a]-pyrrolo[2,1-c]pyrazine Proceeding in a manner analogous to that described in Example 1 and by cyclization of N-(2R-2-hydroxy-2-carbethoxy-isovaleryl)-L-valyl-L-proline-p-nitrophenyl ester, the pure title compound is obtained; M.P. 103°–104°; $[\alpha]_D^{20} = +6°$ (c = 1, ethanol).

The N-(2R-2-hydroxy-2-carbethoxy-isovaleryl)-L-valyl-L-proline and the p-nitrophenyl ester thereof, used as starting materials, are obtained in a manner analogous to steps (d) and (e) of Example 1. S-(+)-isopropyl-benzyloxymalonic acid monoethyl ester chloride and L-valine-benzyl ester are condensed as reaction components in step (a). The intermediates of the individual steps are obtained in resinous form and cannot be obtained in crystalline form.

The following compounds of formula I may also be produced in a manner analogous to that described in Example 1, by cyclization of a compound of formula II. The melting points indicated in the Table refer to compounds of formula I crystallized from isopropyl ether.

The compounds of formula III, used as starting material, may also be obtained in a manner analogous to step (d), and the compounds of formula II, in a manner analogous to step (e) of Example 1, using a compound of formula VIII and a compound of formula VII in step (a) as starting materials.

| Example | Compound I | M.P. | $[\alpha]_D^{20}$ | Starting materials III and II | Compound VII with compound VIII in accordance with step a) of Example 1 |
|---|---|---|---|---|---|
| 7 | 2-carbethoxy-2-methyl-5-isopropyl-10b-hydroxy-3,6-dioxo-octahydro-8H-oxazolo-[3,2-a]pyrrolo[2,1-c]pyrazine | 104–105° | −7° (c = 2, ethanol) | N-(2R-2-hydroxy-2-carbethoxy-propionyl)-L-valyl-L-proline and the p-nitrophenyl ester thereof | S-(+)-methyl-benzyloxymalonic acid monoethyl ester chloride (VIIa) with L-valine benzyl ester |
| 8 | 2-carbethoxy-2,5,5-trimethyl-10b-hydroxy-3,6-dioxo-octahydro-8H-oxazolo[3,2-a]-pyrrolo[2,1-c]pyrazine | 111–113° | +42.7° (c = 1, ethanol) | N-(2R-2-hydroxy-2-carbethoxy-propionyl)-α-methylalanyl-L-proline and the p-nitrophenyl ester thereof | VIIa with α-methylalanine benzyl ester |
| 9 | 2-carbethoxy-2-methyl-5-isobutyl-10b-hydroxy-3,6-dioxo-octahydro-8H-oxazolo-[3,2-a]pyrrolo[2,1-c]pyrazine | 100–101° | −21° (c = 1, ethanol) | N-(2R-2-hydroxy-2-carbethoxy-propionyl)-L-leucyl-L-proline and the thereof | VIIa with L-leucine benzyl ester |
| 10 | 2-carbethoxy-2-methyl-5-(p-methoxybenzyl)-10b-hydroxy-3,6-dioxo-octahydro-8H-oxazolo[3,2-a]pyrrolo-[2,1-c]pyrazine | 156–158° | −23° (c = 1, pyridine) | N-(2R-2-hydroxy-2-carbethoxy-propionyl)-L-(p-methoxy)phenyl-alanyl-L-proline and the p-nitrophenyl ester thereof | VIIa with L-(-p-methoxy)-phenylalanine benzyl ester |
| 11 | 2-carbethoxy-2,5β-dimethyl-5α-benzyl-10b-hydroxy-3,6-dioxo-octahydro-8H-oxazolo[3,2-a]-pyrrolo[2,1-c]pyrazine | 115–117° | +70° (c = 1, ethanol) | N-(2R-2-hydroxy-2-carbethoxy-propionyl)-L-α-methyl-phenylalanyl-L-proline and the p-nitro-phenyl ester thereof | VIIa with L-α-methyl-phenylalanine benzyl ester |
| 12 | 2-carbethoxy-2,10a-dimethyl-5-benzyl-10b-hydroxy-3,6-dioxo-octahydro-8H-oxazolo[3,2-a]-pyrrolo[2,1-c]pyrazine | 112–114° | +20.8° (c = 1, ethanol) | N-(2R-2-hydroxy-2-carbethoxy-propionyl)-L-phenylalanyl-L-α-methyl-proline-p-nitrophenyl ester and the p-nitro phenyl ester thereof | VIIa with L-phenylalanine benzyl ester and in step c) + L-α-methyl-proline benzyl ester |
| 13 | 2-carbethoxy-2-ethyl-5-benzyl-10b-hydroxy-3,6-dioxo-octa-hydro-8H-oxazolo[3,2-a]pyrrolo-[2,1-c]pyrazine | 161–163° | −15.7° (c = 1, pyridine); −21.6° (c = 1, ethanol) | N-(2R-2-hydroxy-2-carbethoxy-butyryl)-L-phenylalanyl-L-proline and the p-nitrophenyl ester thereof | S-(+)-ethyl-benzyloxymalonic acid monoethyl ester chloride (VIIb) with L-phenylalanine benzyl ester |
| 14 | 2-carbethoxy-2-ethyl-5-isopropyl-10b-hydroxy-3,6-dioxo-octahydro-8H-oxazolo[3,2-a]-pyrrolo[2,1-c]pyrazine | 94–95° | +0.8° (c = 2, ethanol) | N-(2R-2-hydroxy-2-carbethoxy-butyryl)-L-valyl-L-proline and the p-nitrophenyl ester thereof | VIIb with L-valine benzyl ester |
| 15 | 2-carbethoxy-2-ethyl-5-iso-butyl-10b-hydroxy-3,6-dioxo-octahydro-8H-oxazolo[3,2-a]-pyrrolo[2,1-c]pyrazine | 94–96° | −3.5° (c = 1, methylene chloride); −5.2° (c = 2, ethanol) | N-(2R-2-hydroxy-2-carbethoxy-butyryl)-L-leucyl-L-proline and the p-nitrophenyl ester thereof | VIIb with L-leucine benzyl ester |
| 16 | 2-carbethoxy-2-isopropyl-5α-benzyl-5β-methyl-10b-hydroxy-3,6-dioxo-octahydro-8H-oxazolo[3,2-a]pyrrolo-[2,1-c]pyrazine | 196° | +68° (c = 1, ethanol) | N-(2R-2-hydroxy-2-carbethoxy-isovaleryl)-L-α-methyl-phenylalanyl-L-proline and the p-nitro-phenyl ester thereof | S-(+)-isopropyl-benzyloxymalonic acid monoethyl ester chloride (VIIc) with L-α-methylphenylalanine benzyl ester |

| Example | Compound I | M.P. | $[\alpha]_D^{20}$ | Starting materials III and II | Compound VII with compound VIII in accordance with step a) of Example 1 |
|---|---|---|---|---|---|
| 17 | 2-carbethoxy-2-isopropyl-5-n-propyl-10b-hydroxy-3,6-dioxo-octahydro-8H-oxazolo[3,2-a]-pyrrolo[2,1-c]pyrazine | 109–110° | +27° (c = 2, dimethyl formamide) | N-(2R-2-hydroxy-2-carbethoxy-isovaleryl)-L-norvalyl-L-proline and the p-nitrophenyl ester thereof | VIIc with L-norvaline benzyl ester |
| 18 | 2-carbethoxy-2-isopropyl-5-sec.butyl-10b-hydroxy-3,6-dioxo-octahydro-8H-oxazolo-[3,2-a]pyrrolo[2,1-c]pyrazine | 103–104° | +20° (c = 1, ethanol) | N-(2R-2-hydroxy-2-carbethoxy-isovaleryl)-L-isoleucyl-L-proline and the p-nitrophenyl ester thereof | VIIc with L-isoleucine benzyl ester |
| 19 | 2-carbethoxy-2-isopropyl-5-isobutyl-10b-hydroxy-3,6-dioxo-octahydro-8H-oxazolo-[3,2-a]pyrrolo[2,1-c]pyrazine | 99–100° | −6.3° (c = 2, pyridine); carbethoxy-isovaleryl)-L- −0.5° (c = 2, ethanol) | N-(2R-2-hydroxy-2-L-leucine leucyl-L-proline and the p-nitrophenyl ester thereof | VIIc with benzyl ester |
| 20 | 2-carbethoxy-2-n-propyl-5,5-dimethyl-10b-hydroxy-3,6-dioxo-octahydro-8H-oxazolo-[3,2-a]pyrrolo[2,1-c]pyrazine | 88–89° | +42° (c = 2, ethanol) | N-(2R-2-hydroxy-2-carbethoxy-n-valeryl)-α-methylalanyl-L-proline and the p-nitrophenyl ester thereof | S-(+)-n-propyl-benzyloxymalonic acid monoethyl ester chloride (VII d) with α-methylalanine benzyl ester |
| 21 | 2-carbethoxy-2-ethyl-5,5-dimethyl-10b-hydroxy-3,6-dioxo-octahydro-8H-oxazolo-[3,2-a]pyrrolo[2,1-c]pyrazine | 110–111° | +45.5° (c = 1, ethanol) | N-(2R-2-hydroxy-2-carbethoxy-butyryl)-α-methylalanyl-L-proline and the p-nitrophenyl ester thereof | VIIb with α-methyl-alanine benzyl ester |
| 22 | 2-cyano-2,5-diisopropyl-10b-hydroxy-3,6-dioxo-octahydro-8H-oxazolo[3,2-a]pyrrolo[2,1-c]-pyrazine | amorphous | — | N-(2S-2-hydroxy-2-cyano-isovaleryl)-L-valyl-L-proline and the p-nitrophenyl ester thereof | S-isopropyl-cyano-benzyloxy-acetyl-chloride with L-valine benzyl ester |
| 23 | 2-carboxamido-2-methyl-5-benzyl-10b-hydroxy-3,6-dioxo-octahydro-8H-oxazolo[3,2-a]pyrrolo[2,1-c]-pyrazine | amorphous | — | N-(2S-2-hydroxy-2-carb-oxamido-propionyl)-L-phenylalanyl-L-proline and the p-nitrophenyl ester thereof | S-methyl-hydroxy-malonic acid mono amide* with L-phenylalanine benzyl ester |

*(Compound VI)

EXAMPLE 24

2-carbethoxy-2-methyl-5-benzyl-10b-hydroxy-3,6-dioxo-octahydro-oxazolo[3,2-a]-pyrrolo[2,1-c]pyrazine 527 mg of N-(2R-2-hydroxy-2-carbethoxypropionyl)-L-phenylalanyl-L-proline-p-nitrophenyl ester are dissolved in 40 cc of dioxane at 20° and 10 cc of an aqueous sodium hydrogen carbonate/sodium carbonate solution (pH = 10) are added. After three hours, dilution is effected with 100 cc of methylene chloride and 50 cc of a 2 normal sodium carbonate solution and extraction is effected thrice with 50 cc of methylene chloride. The organic phase is washed thrice with a 2 normal sodium carbonate solution, is dried over sodium sulphate and concentrated by evaporation. The residue is chromatographed on a 50-fold quantity of silica gel, whereby the title compound is eluted with 1% of methanol in methylene chloride. The title compound crystallizes from isopropyl ether in the form of colourless needles having a M.P. of 134°–136°; $[\alpha]_D^{20} = -34°$ (c = 0.5, pyridine).

The N-(2R-2-hydroxy-2-carbethoxy-propionyl)-L-phenylalanyl-L-proline-p-nitrophenyl ester, used as starting material, is produced as follows:

a.
N-(2R-2-benzyloxy-2-carbethoxy-propionyl)-L-phenylalanyl-L-proline-benzyl ester 4.47 g (10 millimols) of L-phenylalanyl-L-proline-benzyl ester · hydrobromide are dissolved in 100 cc of absolute methylene chloride, 2.5 g (10 millimols) of S-(+)-methyl-benzyloxy-malonic acid monoethyl ester chloride and subsequently 20 cc of absolute pyridine are added at −40° while stirring. After heating to 0°, the mixture is kept at this temperature for 15 hours. Working up is effected by shaking the reaction mixture well with 50 cc of a saturated sodium carbonate solution and washing with water. After extracting with 100 cc of methylene chloride, the combined organic phases are dried and concentrated by evaporation in a vacuum. The title compound crystallizes after taking up the residue in ether; M.P. 120°–121°; $[\alpha]_D^{20} = -12°$ (c = 1, pyridine).

b.
N-(2R-2-hydroxy-2-carbethoxy-propionyl)-L-phenylalanyl-L-proline 2.2 g of the ester obtained in step (a) above are hydrogenated in 50 cc of glacial acetic acid and 50 cc of ethanol with 1 g of palladium/charcoal (10% palladium) at room temperature and normal pressure. After filtration, the filtrate is concentrated by evaporation, whereby the last traces of glacial acetic acid are removed with xylene.

c.
N-(2R-2-hydroxy-2-carbethoxy-propionyl)-L-phenylalanyl-L-proline-p-nitrophenyl ester 406 mg (1 millimol) of the resulting foam are dissolved in 50 cc of methylene chloride, 0.8 cc of absolute pyridine (10 millimols) and 325 mg of di-p-nitrophenyl sulphite are added. After allowing to stand over night at 0°, extraction is effected as usual with sodium hydrogen carbonate/methylene chrloride.

After concentrating the extract which has been dried with sodium sulphate, the title compound crystallizes directly from methylene chloride/isopropyl ether; M.P. 122°–123°; $[\alpha]_{546}^{20} = -67.8°$ (c = 0.4, chloroform).

We claim:

1. A process for the production of a compound of Formula I:

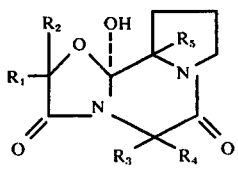

where
- $R_1$ is cyano or -COX,
- X is amino or O-(lower)alkyl of 1 to 6 carbon atoms,
- $R_2$ is lower alkly of 1 to 5 carbon atoms,
- $R_3$ is hydrogen of lower alkyl or 1 to 5 carbon atoms,
- $R_4$ is hydrogen, lower alkyl of 1 to 6 carbon atoms, phenyl benzyl, or benzyl monosubstituted with lower alkoxy of 1 to 4 carbon atoms, and
- $R_5$ is hydrogen or lower alkyl of 1 to 5 carbon atoms which comprises the step of cyclizing a compound of formula II:

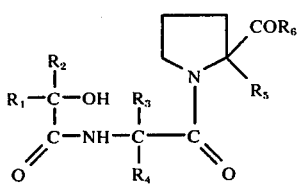

where
$R_1$, $R_2$, $R_3$, $R_4$, and $R_5$ are as defined above and
$R_6$ is phenyloxy or phenyloxy substituted with fluorine, chlorine, mono- or di-nitro, or lower alkyl of 1 to 6 carbon atoms phenylthio or phenylthio substituted with fluorine, chlorine, mono- or di-nitro or lower alkyl of 1 to 6 carbon atoms or N-succinimidoxy by intramolecular condensation in an aprotic polar solvent in the present of a base capable of deprotonizing the nitrogen atom adjacent to

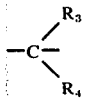

and not reactive with the carbonyl groups or in an aqueous solution at a pH of from 8 to 10.

2. A process according to claim 1 for the production of a compound of formula I:

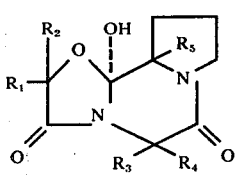

where
- $R_1$ is cyano or -COX,
- X is amino or O-(lower) alkyl of 1 to 6 carbon atoms,
- $R_2$ is lower alkyl of 1 to 5 carbon atoms,
- $R_3$ is hydrogen or lower alkyl of 1 to 5 carbon atoms,
- $R_4$ is hydrogen, lower alkyl of 1 to 6 carbon atoms, phenyl, benzyl, or benzyl monosubstituted with lower alkoxy of 1 to 4 carbon atoms, and
- $R_5$ is hydrogen or lower alkyl of 1 to 5 carbon atoms which comprises the step of cyclizing in a solvent selected from dimethyl sulphoxide, hexamethyl phosphoric acid triamide, acetonitrile, dimethylacetamide and dimethylformamide a compound of formula II:

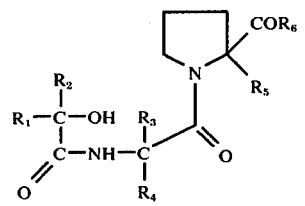

where
$R_1$, $R_2$, $R_3$, $R_4$, and $R_5$ are as defined above and
$R_6$ is o,p-dinitrophenoxy, o-methyl-o',p-dinitrophenoxy, pentachlorophenoxy or p-nitrophenoxy by intramolecular condensation in the presence of sodium hydride or sodium ethylate at a temperature of from 0° to 30° C.

3. A process according to claim 1 for the production of a compound of formula I:

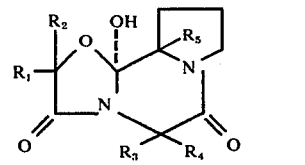

where
- $R_1$ is cyano or -COX,
- X is amino or O-(lower) alkyl of 1 to 6 carbon atoms,
- $R_2$ is lower alkyl of 1 to 5 carbon atoms,
- $R_3$ is hydrogen or lower alkyl of 1 to 5 carbon atoms,
- $R_4$ is hydrogen, lower alkyl of 1 to 6 carbon atoms, phenyl, benzyl, or benzyl monosubstituted with lower alkoxy of 1 to 4 carbon atoms, and
- $R_5$ is hydrogen or lower alkyl of 1 to 5 carbon atoms which comprises the step of cyclizing in an aqueous solution at a pH of from 8 to 10 a compound of formula II:

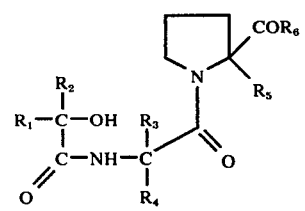

where
$R_1$, $R_2$, $R_3$, $R_4$, and $R_5$ are as defined above and $R_6$ is o,p-dinitrophenoxy, o-methyl-o',p-dinitrophenoxy, pentachlorophenoxy or p-nitrophenoxy at a temperature of from 0° to 30° C.

4. A process according to claim 1, wherein $R_6$ is pentafluorophenoxy, pentachlorophenoxy, phenylthio, p-chlorophenylthio, nitrophenoxy or nitrophenoxy mono- or disubstituted by nitro and/or methyl or chlorine or N-succinimidoxy.

5. A process according to claim 1, wherein $R_6$ is o,p-dinitrophenoxy, o-methyl-o',p-dinitrophenoxy, pentachlorophenoxy or p-nitrophenoxy.

6. A process according to claim 1, wherein $R_2$ is methyl, ethyl or isopropyl, $R_4$ is isopropyl, sec-butyl, isobutyl or benzyl and $R_3$ and $R_5$ are hydrogen.

7. A process according to claim 1 carried out at from 0° to 30°.

8. A process according to claim 1, wherein the resulting compound of formula I is converted to the corresponding acid of the formula,

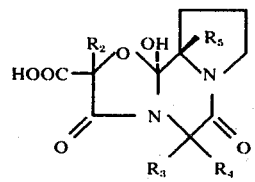

wherein $R_2$ to $R_5$ are as defined in claim 1.

9. A process according to claim 1, wherein the compound of formula II is obtained by reacting an acid of formula III,

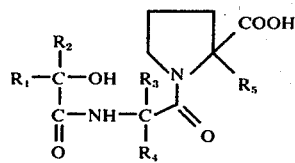

wherein the variables $R_1$ to $R_5$ are as defined in claim 1, with a compound of formula IV, $R_6H$  IV wherein $R_6$ is as defined in claim 1, or with a compound of formula IVa,

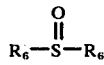

wherein $R_6$ is as defined in claim 1.

10. A process according to claim 1, wherein the solvent is dimethyl sulphoxide, hexamethyl phosphoric acid triamide, acetonitrile dimethylacetamide or dimethylformamide.

11. A process according to claim 10, wherein the solvent is dimethyl formamide.

12. A process according to claim 1, wherein the strong base is an alkali metal hydride or an alkali metal alcoholate of 1 to 6 carbon atoms.

13. A process according to claim 12, wherein the strong base is sodium hydride or ethylate.

14. A process according to claim 1, wherein the strong base is an alkali metal amide and $R_1$ is cyano or $CONH_2$.

15. A process according to claim 1 carried out in the presence of 1 to 1.5 mols of strong base per mol of compound of formula II.

16. A process according to claim 1 carried out in an aqueous solution at a pH of from 8 to 10.

17. A process according to claim 16 carried out in water and a solvent selected from dimethyl sulphoxide dioxane, tetrahydrofuran, dimethoxyethane, dimethylformamide or dimethylacetamide.

18. A process according to claim 17 carried out in water and dioxane.

19. A process according to claim 16 carried out in the presence of a borate buffer and 2-hydroxy-pyridine.

20. A process according to claim 16 carried out in the presence of a sodium hydrogen carbonate/sodium carbonate solution.

21. A compound of formula I:

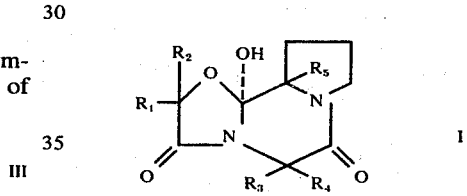

where
$R_1$ is CN or $CONH_2$,
X is amino or O-(lower) alkyl of 1 to 6 carbon atoms,
$R_2$ is lower alkyl of 1 to 5 carbon atoms,
$R_3$ is hydrogen or lower alkyl of 1 to 5 carbon atoms,
$R_4$ is hydrogen, lower alkyl of 1 to 6 carbon atoms, phenyl, benzyl, or benzyl monosubstituted with lower alkoxy of 1 to 4 carbon atoms, and
$R_5$ is hydrogen or lower alkyl of 1 to 5 carbon atoms.

22. A compound of claim 21, wherein $R_2$ is lower alkyl, $R_3$ is hydrogen or lower alkyl, $R_4$ is hydrogen, lower alkyl, phenyl, benzyl, or benzyl monosubstituted by lower alkoxy, and $R_5$ is hydrogen or lower alkyl.

23. A compound of claim 22, which is 2-cyano-2,5-diisopropyl-10b-hydroxy-3,6-dioxo-octahydro-8H-oxazolo[3,2-a]pyrrolo[2,1-c]pyrazine.

24. A compound of claim 22, which is 2-carboxamido-2-methyl-5-benzyl-b 10b-hydroxy-3,6-dioxooctahydro-8H-oxazolo[3,2-a]pyrrolo [2,1-c]pyrazine.

* * * * *